United States Patent
Ekart et al.

(10) Patent No.: US 6,191,177 B1
(45) Date of Patent: Feb. 20, 2001

(54) DEPOLYMERIZATION APPARATUS FOR RECYCLING POLYESTERS

(75) Inventors: Michael Paul Ekart; Thomas Michael Pell, Jr.; David Dunlap Cornell, all of Kingsport; Damon Bryan Shackelford, Johnson City, all of TN (US)

(73) Assignee: Eastman Chemical Company, Kingsport, TN (US)

( * ) Notice: Under 35 U.S.C. 154(b), the term of this patent shall be extended for 0 days.

(21) Appl. No.: 09/607,213

(22) Filed: Jun. 30, 2000

Related U.S. Application Data

(62) Division of application No. 09/167,248, filed on Oct. 6, 1998, now Pat. No. 6,136,869.
(60) Provisional application No. 60/062,540, filed on Oct. 17, 1997.

(51) Int. Cl.[7] .............................. C08J 11/04; B29B 15/60
(52) U.S. Cl. .................. 521/48.5; 528/481; 528/496; 528/501; 528/503; 526/65; 526/67; 526/71; 425/13
(58) Field of Search .................... 521/48.5; 528/481, 528/496, 501, 503; 526/65, 67, 71; 425/13

(56) References Cited

U.S. PATENT DOCUMENTS

| | | | |
|---|---|---|---|
| 3,037,050 | * | 5/1962 | Helsenberg et al. . |
| 3,321,510 | * | 5/1967 | Lotz et al. . |
| 3,488,298 | * | 1/1970 | Barkey et al. . |
| 3,776,945 | * | 12/1973 | Ligorati et al. . |
| 3,884,850 | * | 5/1975 | Ostrowski . |
| 4,620,032 | * | 10/1986 | Doerr . |
| 5,051,528 | * | 9/1991 | Naujokas et al. . |
| 5,298,530 | * | 3/1994 | Gamble et al. . |
| 5,414,022 | * | 5/1995 | Toot, Jr. et al. . |
| 5,576,456 | * | 11/1996 | Gamble et al. . |
| 5,635,584 | * | 6/1997 | Ekart et al. . |

* cited by examiner

Primary Examiner—Samuel A. Acquah
(74) Attorney, Agent, or Firm—Harry Gwinnell; Karen Harding

(57) ABSTRACT

An apparatus for depolymerizing recycled polyester into its component ester monomers and half esters includes a first reactor for depolymerizing the recycled polyester, a separator for separating ester monomeric components and half-esters from secondary materials produced in the first reactor, and a second reactor for producing a low molecular weight polyester from liquefied separator products.

6 Claims, 1 Drawing Sheet

DEPOLYMERIZATION APPARATUS FOR RECYCLING POLYESTERS

CROSS-REFERENCE TO RELATED APPLICATIONS

This application is a divisional of the application have U.S. Pat. Ser. No. 09/167,248 filed Oct. 6, 1998, now U.S. Pat. No. 6,136,869, from which benefit is claimed to the earlier filed provisional application having U.S. Ser. No. 60/062,540 filed Oct. 17, 1997, the entire disclosure of which is incorporated herein by reference.

FIELD OF THE INVENTION

This invention relates to polyesters and more particularly to an improved process for using recycled polyesters. The improved process requires little purification equipment and can handle variable post consumer feedstock or other recyclable polyester materials besides polyethylene terephthalate (PET).

BACKGROUND OF THE INVENTION

Polyester resins have widespread utility in a variety of applications, such as films, thermoforming, and blow molding. Additionally, polyesters have widespread acceptance and use in today's consumer products. Polyesters, such as PET and polyethylene naphthalate (PEN), are used in disposable products such as food and beverage contains, and especially carbonated drink containers, photographic film, magnetic tape, and the like.

In an effort to conserve resources, several methods have been disclosed in the literature for recycling polyesters. Some methods involve depolymerization, i.e., breaking the ester bond and reducing the polymer to its monomer components. Others processes blend virgin polymer with postconsumer waste materials. These latter processes tend to be simpler and the equipment is less expensive. However, these simpler processes are not without their problems. These processes cannot remove many of the variable constituents, such as colorants and catalyst metals, present in postconsumer polyesters.

Depolymerization of post-consumer polyester into its monomeric components offers more promise since the monomers can in some cases be purified by techniques well known in the art such as distillation, crystallization and filtration. The pure recycle monomers can subsequently be fed to a polyester production process. The cost of the purification steps, however, can make the recycle monomers more expensive than virgin raw materials.

Various methods have been disclosed in the literature for depolymerization of post-consumer polyesters into their component monomers, such as ethylene glycol and terephthalic acid, naphthalic acid or their derivatives, so they could be reused.

For example, U.S. Pat. No. 3,037,050 discloses the recovery of terephthalate acid dimethyl ester by treating polyethylene terephthalate in the form of bulky or lumpy solid masses with super-heated methanol vapor in the presence of any suitable transesterification catalyst substantially at atmospheric pressure.

U.S. Pat. No. 3,321,510 discloses a process for decomposing polyethylene terephthalate by treating with steam at a temperature of from about 200° C. to 450° C. The steam-treated polyethylene terephthalate is then reduced from a brittle solid product to a powder having a mean particles size of from about 0.0005 to 0.002 millimeters, after which the fine powder is atomized with a gaseous substance including inert gas and methanol vapor to from an aerosol. The aerosol is conducted through a reaction zone at a temperature of 250° C. to 300° C. in the presence of excess methanol vapors.

U.S. Pat. No. 3,776,945 discloses a process of depolymerizing polyethylene terephthalate waste to obtain dimethyl terephthalate and ethylene glycol. The waste is subdivided into dimensions between 4 and 35 mesh and treated at a temperature of 100° C. to 300° C. in the presence of acid catalysts. The proportion of methanol to waste is between 1:1 by weight.

U.S. Pat. No. 4,620,032 teaches an extrusion process for reducing the reaction time in the hydrolysis of polyesters by intimately admixing with the molten polyester a depolymerizing agent which is either one of the products resulting from the complete hydrolytic depolymerization of the polyester or water.

U.S. Pat. No. 5,051,528 issued to Naujokas, et al on Sep. 24, 1991, discloses a method for recovering ethylene glycol and dimethyl terephthalate (DMT) from polyethylene terephthalate polymers (PET). The process includes the steps of dissolving scrap polyester in oligomers of ethylene glycol and terephthalate acid or dimethyl terephthalate and passing super-heated methanol through the solution. The ethylene glycol and dimethyl terephthalate are subsequently recovered overhead. The patent teaches that an oligomer of the same monomers is that of the monomers which form the constituent parts of the polymer, that is, the oligomer is formed from ethylene glycol and terephthalic acid or dimethyl terephthalate. Accordingly, the oligomer is any low molecular weight polyester polymer of the same composition as that of the scrap material being employed as the starting component so that the scrap polymer will dissolve in the low molecular weight oligomer.

U.S. Pat. No. 5,298,530 issued to Gamble, et al on Mar. 29, 1994, discloses a process of recovering components from PET having the steps of introducing glycol and terephthalic acid or dimethyl terephthalate oligomers to a first vessel and heating the oligomers, introducing scrap polyesters to the first vessel and forming a start-up melt with the oligomers, transferring the melt from the first vessel to a second vessel, passing super-heated methanol through the melt in the second vessel to form a final melt comprising low molecular weight polyesters in monomers, transferring the final melt from the second vessel to the first vessel, and recovering components in the form of a vapor stream exiting the second vessel. The process shortens the length of the polyester chain in a polyester scrap melt prior to the introduction of the scrap melt to a first reactor.

U.S. Pat. No. 5,414,022 discloses an improvement to the process of U.S. Pat. No. 5,051,528. The improvement includes the steps of adding polyester to the dissolver and combining it with melt from the reactor and liquid from the rectifier to reduce the chain length of the polyester, transferring the reduced chain length polyester from the dissolver to the reactor, passing super-heated methanol through the reactor to depolymerize polyester into its constituent monomers, transferring the depolymerized products from the reactor to the rectifier, and separating the depolymerized products in the rectifier into a vapor phase containing component monomers and a liquid phase containing higher molecular weight materials.

U.S. Pat. No. 5,576,456 issued to Gamble, et al, discloses an improvement to the process disclosed in U.S. Pat. No. 5,298,530 in that the reactor for depolymerizing the polyester into its components uses a staged column reactor for the depolymerization and for separating monomer components from the higher boiling materials. The process further utilizes a reactor in which the continuous phase is the super-heated methanol in the molten polyester and polyester decomposition products are the discontinuous phase.

The processes and equipment described in the prior art employ a reactor in which the polyester is depolymerized in the presence of superheated methanol and from which vapor is removed. The methanol stream in the reactor can be either the continuous phase or the discontinuous phase. These depolymerization processes also include a rectifier or partial condenser to return any dimer, trimer, or other oligomeric species, as well as other components with high boiling points from the vapor to the reactor.

One will understand that the above processes require the polyester scrap to be reacted with a suitable catalyst and a lower alcohol such as methanol, ethanol, propanol and the like at elevated temperatures and pressures as are known to those skilled in the polyester art. The ester of the dibasic acid, DMT, is then recovered by a rather complex and time consuming operation. Half-esters such as methyl hydroxyethyl terephthalate (MHET) are incompatible with the DMT purification process and were heretofore returned to the depolymerization reactor for further processing, otherwise the MHET is lost.

A problem with the all of the above processes for recycling polyester and particularly PET is that the recovered material must be in the form of dimethyl terephthalate (DMT) and ethylene glycol. The reason for this is that DMT, which is reacted with ethylene glycol to form diglycol terephthalate which is then polycondensed to form PET, can be purified using techniques, such as distillation and crystallization, known to those skilled in the art.

Thus, there is a widespread need for a simple and economical method that will permit the recycling of polyesters for recovering suitable feedstock material that may be used in either a terephthalic acid (TPA) based polyester manufacturing process or a DMT polyester manufacturing process. Desirably, such process may recover at least a portion of the monomer constituents from the depolymerization of the polyester.

SUMMARY OF THE INVENTION

One principle advantage of the present invention is that it is not necessary to return "half esters" (esters of dicarboxylic acids with methanol and a glycol from which the polyester is composed) to the reactor for further depolymerization into the monomeric components of glycol and DMT.

Broadly, the present invention provides a process for recovering from recycled polyester a material suitable for polyester feedstock which may be used in either a TPA or DMT based polyester manufacturing process. The process includes the steps of depolymerizing the recycled polyester into a product having component monomers and half-esters from secondary materials such as colorants, pigments and the like and mixing the component monomers and half-esters under transesterification conditions. This latter step, advantageously and unexpectedly, produced a low molecular weight polyester that can be used in either a TPA based polyester manufacturing process without any deleterious effects on either the process or the polyester product.

In a preferred embodiment, the process includes contacting the recycled polyester in a dissolver with oligomers of the same monomers as present in the recycle polyester to produce a solution or melt; contacting the solution with a super-heated lower alkyl alcohol to depolymerize the polyester into a product having ester monomers and half-esters; and under transesterification conditions, mixing the product with one or more monomers to produce a low molecular weight polyester.

Another aspect of the invention is for an apparatus for practicing the process of the present invention. The apparatus includes a first reactor operated under depolymerization conditions, a separator means for separating ester monomers, and half-ester products produced from the first reactor from secondary materials, and a second reactor operated under transesterification conditions. The second reactor receives, as part of its feed, condensed ester monomers and half-ester products from the separator means to produce a low molecular weight polyester. In a preferred embodiment of the invention, additional component monomers are added to the second reactor during the transesterification process. It is to be understood that although expressed singularly, it is within the scope of the invention described herein that additional reactors and separators may be used to produce the low molecular weight polyester.

In a preferred embodiment, the apparatus includes a dissolver for at least partially solubilizing or forming a melt of the solid polyester prior to feeding the polyester to the first reactor.

Another advantage of the present process is that it requires less equipment for recycling of the polyesters than what has been previously taught.

Another advantage of the present invention is that the low molecular weight polyester product can be used in either a TPA or DMT based polyester process.

It is an object of the invention to provide a process for recovering a material suitable for polyester feedstock from recycled polyester.

Another object of the invention is to provide a process for recovering a material that is suitable as a feedstock in either a TPA or DMT based polyester manufacturing process.

It is another object of the invention to provide an apparatus for recycling polyester and recovering a material suitable for polyester feedstock from recycled polyester.

These and other objects and advantages will become more readily apparent those skilled in the art when considered with reference to the following specification and the accompanying drawing. It is to be understood that the embodiments described herein are for illustrative purposes only and inventive concept is not to be considered limited thereto.

DETAILED DESCRIPTION OF THE PREFERRED EMBODIMENTS

Figure 1:
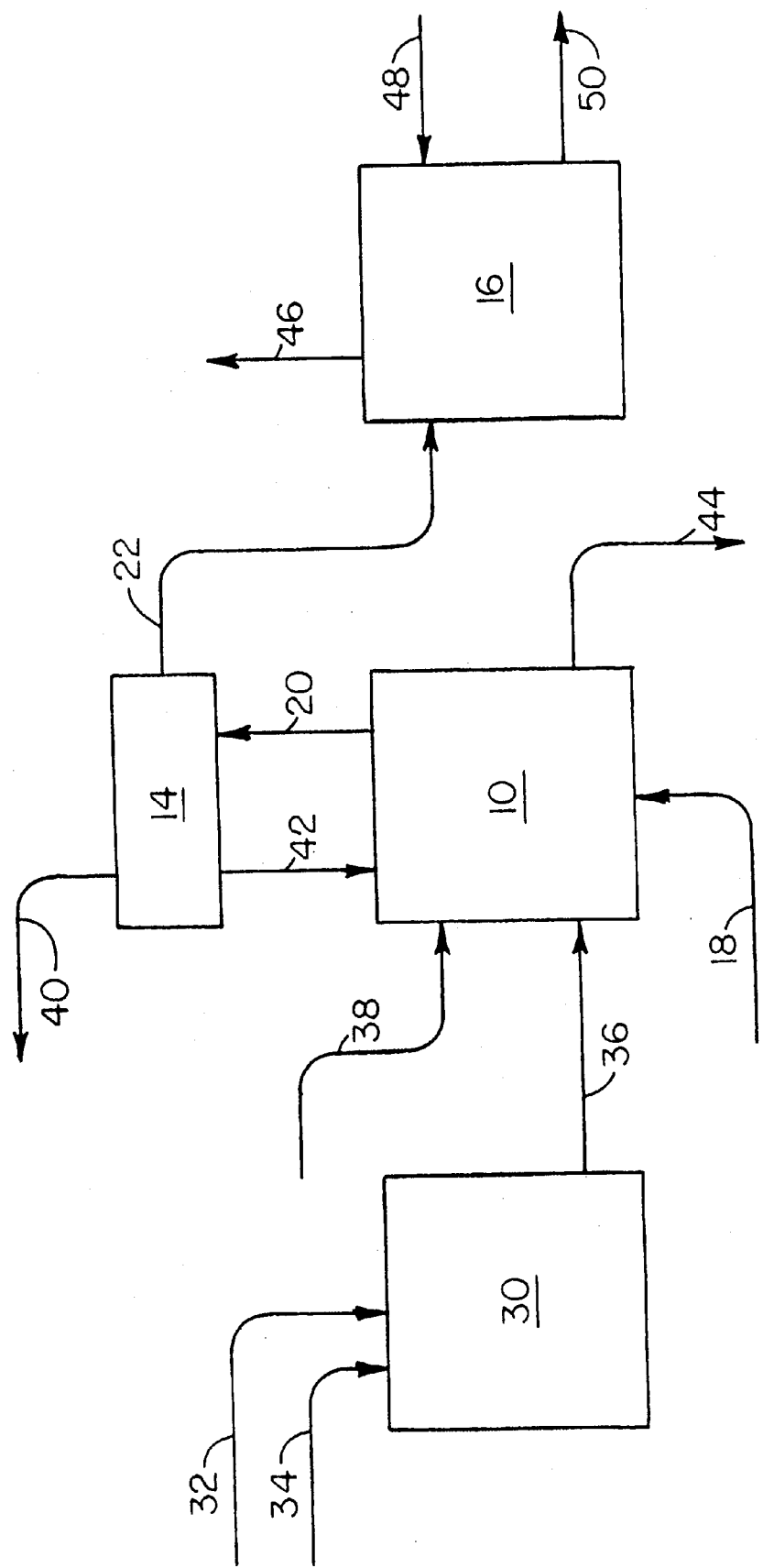
FIG. 1 is a schematic flow diagram illustrating the process of the invention.

The feedstock for the process of the invention can be any polyester waste, which, for example, may be post-consumer material, scrap from polyester resin production processes, scrap from processes that form polyester articles, polyester articles rejected because they do not meet specifications, and the like.

For purposes of describing the present invention, the depolymerization and re-polymerization of PET is described in greater detail. However, it will be apparent to one skilled in the art the process is suitable for other polyesters. For example, polymers that are particularly useful in this process besides PET include PEN, and copolyesters containing up to about 50 mole % of modifying dibasic acids and/or glycols and blends thereof. Modifying dibasic acids may contain from about 2 to about 40 carbon atoms and include isophthalic, adipic, glutaric, azelaic, sebacic, fumaric, cis- or trans-1,4-cyclohexanedicarboxylic, the various isomers of naphthalene dicarboxylic acids and mixtures thereof. Highly useful naphthalene dicarboxylic acids include the 2,6-, 1,4-, 1,5-, or 2,7- isomers but the 1,2-, 1,3-, 1,6-,1,7-, 1,8-, 2,3-, 2,4-, 2,5-, and/or 2,8- isomers may also be used. The dibasic acids may be used in acid form or as their esters such as the dimethyl esters for example.

Typical modifying glycols may contain from about 3 to about 10 carbon atoms and include propylene glycol, 1,3-propanediol, 1,4-butanediol, 1,6-hexanediol, diethylene glycol, 1,4-cyclohexanediol, 1,4-cyclohexanedimethanol, and the like. The 1,4-cyclohexanedimethanol may be in the cis or the trans form or as cis/trans mixtures.

With reference to FIG. 1, where a preferred apparatus is schematically illustrated for carrying out the process of the invention, which may be carried out in either a continuous or batch wise operation. The apparatus includes a first reactor 10, a rectifier 14, and a second reactor 16. The various components of the apparatus are connected together by pipes, pumps, storage tanks, and valves (not shown) as needed to transfer the reactants from one location to another in accordance with the process. The apparatus can further include scrubbers, condensers, reboilers, and the like (not shown) known to those skilled in the distillation art.

Referring to FIG. 1 in greater detail, the recycle PET polyester 38 in an appropriate form and size is fed to the first reactor 10 by any suitable means, such as a pressurized pipe, gravity feed system, rotary feed system, or extruder and can be a powder, flake or melt. The first reactor 10 may be a staged column and can include packing or trays over which the PET is distributed, thereby increasing the surface area that can come in contact with the lower alkyl alcohol. A thin film or wiped film reactor may also be employed and still obtain the operational advantages of this invention. Typically, in a continuous operation such as in a staged column, the polyester is added toward the top of the first reactor 10 flows toward the bottom of the first reactor 10 by gravity.

Alternatively, the first reactor 10 may be a vessel having an agitator, a temperature control means, such as, a steam jacket or other thermal transfer medium that are well known in the art, and a means for contacting a lower alkyl alcohol, with the recycled polyester to depolymerize the polyester. An example of such a reactor is described in U.S. Pat. No. 5,051,528, the entire disclosure of which is incorporated herein by reference.

Added to the first reactor 10 is a sufficient amount of a lower alkyl alcohol 18, such as methanol, ethanol, propanol and mixtures thereof with the preferred alcohol being methanol, to depolymerize the PET. When the lower alkyl alcohol is methanol, it is added to the reactor in an amount of from about 1 part by weight to about 10 parts by weight methanol per part of polyester and more preferably, from about 2 parts by weight to about 6 parts by weight methanol per part of polyester, and most preferably, from about 3 parts to about 5 parts by weight methanol per part of polyester.

The methanol 18 may be introduced to the first reactor 10 as a super-heated vapor or as a liquid. The methanol 18 can also be provided to the first reactor 10 using conventional means known to those skilled in the art. Desirably, depolymerization of the polyester is essentially completed in the first reactor 10. The first reactor 10 is operated under a temperature of about 220° C. to about 300° C. and preferably, from about 240° C. to about 300° C. The temperature of the methanol fed to the first reactor 10 can range from ambient temperature to about 240° C., and desirably, ranges from about 200° to about 300° C. and preferably is a super heated vapor at a temperature of from about 240° C. to about 300° C. The operating pressure of the first reactor 10 can range from about atmospheric up to about 80 bar and preferably up to about 10 bar.

An ester-exchange catalyst may be added in suitable amounts to the first reactor 10 to speed the depolymerization reaction. Such catalysts are well known in the art and include compounds of manganese, zinc, titanium, lithium, magnesium, calcium, or cobalt.

A purge stream 44 to remove nonvolatile components such as high boiling impurities and reaction by-products may be included on the first reactor 10. Depending on the specific composition of this purge stream, it can be discarded, recycled or sent to an additional process not part of this invention for recovery of specific components.

At the bottom of the first reactor 10 there can optionally be located a reboiler (not shown) which provides energy to the first reactor 10. The reactor melt can be withdrawn toward the bottom of the reactor, heated and reintroduced toward the top of the reactor. Use of such a reboiler to heat the contents of the reactor permits adjusting the operation of the column without being dependent on a minimum amount of dissolver melt being introduced to the first reactor 10.

In a preferred embodiment, the apparatus includes a dissolver 30 for at least partially solubilizing the PET 32 prior to its introduction into the first reactor 10. The recycled PET 32 is contacted with oligomers 34 of the same component monomers as the polyester so as to at least partially solubilize the polyester. In the case where the polyester is PET, the oligomers would be those of ethylene glycol, terephthalic acid or dimethyl terephthalate with those of ethylene glycol being the preferred oligomer. In the dissolver 30, desirably, the PET is solubilized and heated so that the dissolver melt 36 can be fed to the first reactor 10 for depolymerization by contacting the dissolver melt with methanol 18. Relative to atmospheric pressure, the dissolver 30 can be run at a negative pressure, equal pressure, or at a slightly positive pressure. The dissolver 30 is equipped with a means for heating its contents to a temperature of about 210° C. to about 260° C. Preferably, the dissolver 30 is maintained at a temperature in the range of 240° to 260° C.

Optionally, an ester exchange catalyst, such as zinc acetate, can be added to the dissolver 30. If so included, the amount of catalyst added ranges from about 30 to about 300 ppm, relative to the amount of polyester added to the dissolver 30, and preferably from about 30 to 100 ppm, is added to the dissolver 30.

The polyester melt 36 in the dissolver 30 desirably is protected from the atmosphere by a blanket of inert gas. Suitable inert gases include those gases which do not react with the polyester melt 36 in the dissolver 30. Non-limiting examples of suitable inert gases include nitrogen, carbon dioxide, argon, etc. This reduces degradation of the dissolver melt due to oxidation reactions.

Low boiling components which evolve from the dissolver 30 may contain monomers that can be recovered together with the monomers exiting the first reactor 10. This can be accomplished by recovering them in a separate process or apparatus or absorbing them into the liquid glycol added to the dissolver 30

The polyester melt 36 from the dissolver 30 is transferred to the first reactor 10 via means that can be used to control the rate of introduction of these materials. The first reactor 10 can be run at a higher pressure than the dissolver 30, which eliminates the need for additional pump where, in an optional embodiment (not shown), a portion of the reactor melt from the first reactor 10 is returned to the dissolver 30.

The first reactor product stream 20, which can include such materials as dicarboxylic acid esters, lower alkyl alcohols and glycols, including methanol, dimethyl terephthalate, glycols including ethylene glycol, diethylene glycol, and triethylene glycol, dimethylisophthalate, cyclohexanedimethanol, and methylhydroxyethyl terephthalate, exits the first reactor 10 and is transferred to the rectifier 14. Depending upon the operation of the first reactor 10, the product stream 20 may be vaporous, liquid or a combination thereof. The rectifier 14 separates the higher boiling secondary materials 42 from the lower boiling materials in the product stream 20. As used herein the term "secondary materials" means materials less volatile than the monomers, methanol, and half-esters and includes, by way of non-limiting example, colorants, dyes, catalyst metals and other higher molecular weight oligomers.

The rectifier product stream 22 generally includes dimethyl esters of the dicarboxylic acid or acids from which the polyester is composed, component monomers and "half-esters", such as methyl hydroxyethyl terephthalate. Desirably, the DMT and ethylene glycol, if vaporous, are condensed after removal from the rectifier 14. Techniques for condensing vapors are well known to those skilled in the distillation art. For example, the condensation may occur in a heat exchanger, in which the vapor stream is cooled, or in a spray condenser. A series of two or more condensers may also be used. Desirably, the majority of the methanol 40 is removed from the rectifier and returned to the first reactor 10. The mixture of DMT and ethylene glycol in the rectifier product stream 22 is kept above the temperature at which DMT will solidify from the solution, generally above about 165° C. to about 210° C. and at a pressure of from about atmospheric to about 10 bar.

Optionally, a portion of the liquid from the rectifier 14 can be sent back to the dissolver 30. While the rectifier 14 is shown as a separate apparatus, one skilled in the art will understand that the rectifier 14 may comprise additional stages of the first reactor 10 above the point at which dissolver melt is added. Advantageously, the first reactor product stream 20 can be purified using a rectifier 14 but otherwise is substantially free of subsequent purification.

The rectifier product stream 22 is fed to the second reactor 16 where the DMT and ethylene glycol are reacted under transesterification conditions to form MHET, BHET 50, and higher molecular weight oligomers and methanol. The methanol 46 is separated from the other components and purified, if needed, and recycled to the first reactor 10 for use in depolymerization of other polyester feedstock. Excess ethylene glycol 48 may be added to the second reactor 16 to help drive the condensation reaction to completion. The excess glycol may be virgin glycol, recycle glycol or mixtures thereof. Conditions at which the transesterification reaction occurs are well known and generally occur at a temperature of about 190° C. or higher, and at atmospheric pressure or greater. At such conditions, the large majority of methanol produced in the reaction is vaporized and removed from the second reactor 16. An ester exchange catalyst may be added to the second reactor 16 to facilitate the reaction. Examples of such catalysts include compounds or combination of compounds of manganese, zinc, titanium, lithium, magnesium, calcium, or cobalt.

Surprisingly, it has been discovered that DMT and ethylene glycol products removed from the methanolysis reactor, i.e. the first reactor 10, and substantially purified through the rectifier 14, can be recombined to form BHET and oligomers that are suitable for reuse in either a TPA based polyester process or a DMT based polyester process without requiring additional separation equipment such as distillation or reactive distillation columns, or crystallizers as is taught in the prior art. Advantageously, because little purification and separation equipment is needed, the capital cost of the process is reduced. A further advantage of the present invention is that it does not require half esters, such as methyl-2-hydroxyethyl terephthalate (MHET), to be returned to the first reactor 10 to improve yields as is taught by the prior polyester recycling processes.

The mixture of BHET and oligomers produced from recycled polyesters according to the present invention may be fed to any one or more of the reactors in a polyester manufacturing process, including those in which esterification (or transesterification) of dicarboxylic acids (or their dialkyl esters) occurs, or those in which polycondensation occur. Typically, polycondensation catalyst is also added to the process. Well known catalysts include compounds of antimony, titanium, germanium, gallium, tin, and lead. Phosphorus and cobalt compounds may also optionally be present from the beginning of the reaction, or may be added at any convenient point in the process.

The examples which follow are given to better illustrate the inventive concept without in any way limiting it. All parts are given in weight percentages unless specified otherwise.

For the Examples 1–4 below, PET was produced using a 0.5 liter batch reactor. The transesterification and polymerization conditions for each example were the same and are set forth in Table 1 below.

TABLE 1

| Stage | Time (min.) | Temp ° C. | Vacuum (Torr) | Stir (rpm) |
|---|---|---|---|---|
| 1 | 0 | 195 | 760 | 50 |
| 2 | 10 | 190 | 760 | 200 |
| 3 | 70 | 190 | 760 | 200 |
| 4 | 10 | 220 | 760 | 200 |
| 5 | 60 | 220 | 760 | 200 |
| 6 | 15 | 270 | 760 | 200 |
| 7 | 1 | 270 | 400 | 200 |
| 8 | 1 | 270 | 100 | 200 |
| 9 | 30 | 270 | 100 | 200 |
| 10 | 1 | 270 | 10 | 200 |
| 11 | 10 | 270 | 10 | 200 |
| 12 | 15 | 285 | 10 | 200 |
| 13 | 10 | 285 | 0.5 | 200 |
| 14 | 90 | 285 | 0.5 | 200 |

COMPARATIVE EXAMPLE 1

PET was produced by reacting 97 grams of virgin DMT and 65 grams of ethylene glycol in the presence of 220 ppm antimony (as antimony acetate) and 100 ppm manganese (as manganese acetate) to form a BHET/oligomer mixture. A phosphorus stabilizer was then added and the mixture polymerized at elevated temperatures under vacuum. The CDM color of the resulting polymer was similar to those of the polymers produced in Examples 1 and 2 (L*=90.2, a*=−0.1, b*=−0.9).

COMPARATIVE EXAMPLE 2

PET was produced by reacting 75 weight percent virgin materials with 25 weight percent purified recycle materials. The recycled materials were obtained by reacting 200 grams of post-consumer flake with approximately 50% green flake with 400 grams of methanol and a zinc acetate catalyst solution having 150 ppm zinc. The reactants were mixed in a 1 liter autoclave and heated to a temperature of about 240° C. for 2 hours. The depolymerized PET was transferred to a distillation flask and heated. The reaction mixture was boiled and DMT, EG, and methanol vapors were removed.

One part of the resulting DMT and ethylene glycol were reacted with three parts of virgin DMT and ethylene glycol, along with virgin excess ethylene glycol, in the presence of 60 ppm manganese (as manganese acetate) and 225 ppm antimony (as antimony acetate) to form a BHET/oligomer mixture. A phosphorus stabilizer was then added and the mixture polymerized at elevated temperatures under vacuum. The color of the resulting polymer was visibly poor ($L^*=86.5$, $a^*=-9.6$, $b^*=-1.4$). The large negative $a^*$ indicates that the polymer had a greenish color. This example shows that purification steps beyond depolymerization are necessary to provide polymer having good visual properties.

EXAMPLE 1

PET was produced by reacting 75 weight percent virgin materials with 25 weight percent purified recycle materials. The recycled materials were obtained by reacting 200 grams of post-consumer flake with approximately 50% green flake with 400 grams of methanol and a zinc acetate catalyst solution having 150 ppm zinc. The reactants were mixed in a 1 liter autoclave and heated to a temperature of about 240° C. for 2 hours. The depolymerized PET was transferred to a distillation flask and heated. The reaction mixture was boiled and DMT, EG, and methanol vapors were removed through a rectifying column, then condensed.

In forming the PET, 72.83 grams of virgin DMT and 30 grams of DMT derived from the recycled depolymerized PET were mixed with 65 grams of virgin ethylene glycol. This mixture was reacted in the presence of 60 ppm manganese (as manganese acetate) and 225 ppm antimony (as antimony acetate) to form a BHET/oligomer mixture using the transesterification conditions described above. A phosphorus stabilizer was then added and the mixture polymerized at elevated temperatures under vacuum. The CDM color of the resulting polymer was good ($L^*=92.0$, $a^*=-0.3$, $b^*=0.5$). This example illustrates that at least some separation of the reaction mixture from secondary material is necessary to obtain a polymer having a good color property. Surprisingly, good final polymer was generated with only rectification of the reaction mixture. This would not have been expected based upon the teachings of the prior art.

EXAMPLE 2

PET was produced using 100% purified recycled materials obtained using the procedure of Example 1 with the addition of a minor amount of supplemental ethylene glycol to drive the reaction forward. In forming the PET, 102.83 grams of DMT and 65 grams of ethylene glycol were mixed and reacted in the presence of 99 ppm manganese (as manganese acetate) and 217 ppm antimony (as antimony acetate). A phosphorus stabilizer was then added and the mixture polymerized at elevated temperatures under vacuum. The CDM color of the resulting polymer was good ($L^*=91.2$, $a^*=-0.6$, $b^*=-0.9$). Thus good polymer can be made via the present invention from 100% recycled materials without the extensive separation/purification steps required by prior processes.

The invention has been described with reference to specifically described preferred embodiments. One skilled in the art will understand that changes and modifications can be made to the apparatus and process steps specifically described, and it is the intent that the claims cover such modifications and equivalents thereof without departing from the scope and spirit of the invention claimed herein.

We claim:

1. An apparatus for depolymerizing a recycled polyester in accordance with the process of depolymerizing said polyester into a product having ester monomers, glycols and half-esters by contacting said recycled polyester with a lower alkyl alcohol selected from the group consisting of methanol, ethanol, propanol and mixtures thereof; separating said ester monomers, glycols and half-esters from secondary materials in said depolymerized product by rectifying said product but otherwise said ester monomers, glycols and half-esters are substantially free of subsequent purification and separation of said glycols from said ester monomers and half-esters; and mixing said product ester monomers, glycols and half-esters with one or more monomers under transesterification conditions to produce a low molecular weight polyester, wherein said apparatus comprises:

a) a first reactor adapted for receiving said recycled polyester and operated under depolymerizing conditions;

b) a separator receiving depolymerization ester monomers and half-esters products produced from said first reactor and separating said products from secondary materials; and c) a second reactor receiving said products from said separator and being operated under transesterification conditions to produce a low molecular weight polyester.

2. The apparatus of claim 1 further comprising a dissolver for contacting and liquefying said recycled polyester, said dissolver being in liquid communication with said first reactor.

3. The apparatus of claim 2 wherein said separator is a rectifier.

4. The apparatus of claim 3 wherein said rectifier condenses vaporous depolymerization products prior to their being fed to said second reactor.

5. The apparatus of claim 1 wherein said first reactor has super-heated methanol passed through said polyester and carrying vaporized products overhead.

6. The apparatus of claim 1 wherein said second reactor includes a plurality of reactors.

* * * * *